United States Patent [19]

Jayasuriya et al.

[11] Patent Number: 5,703,067
[45] Date of Patent: Dec. 30, 1997

[54] INHIBITORS OF FARNESYL-PROTEIN TRANSFERASE

[75] Inventors: Hiranthi Jayasuriya, Edison; Russell B. Lingham, Watchung, both of N.J.; Fernando Pelaez; Manuel Sanchez, both of Madrid, Spain; Keith C. Silverman, Somerset, N.J.; Sheo Bux Singh, Edison, N.J.; Deborah L. Zink, Manalapan, N.J.

[73] Assignee: Merck & Co., Inc., Rahway, N.J.

[21] Appl. No.: 435,047

[22] Filed: May 8, 1995

[51] Int. Cl.$^6$ .............................. A61K 31/575; C07J 9/00
[52] U.S. Cl. ..................... 514/179; 552/541; 552/560; 552/582
[58] Field of Search ........................ 552/541, 560, 552/582; 514/179

[56] References Cited

U.S. PATENT DOCUMENTS

| | | | |
|---|---|---|---|
| 4,871,727 | 10/1989 | Burg et al. | 514/179 |
| 4,874,755 | 10/1989 | Ashe et al. | 514/179 |
| 5,023,250 | 6/1991 | Adams et al. | 514/179 |
| 5,141,851 | 8/1992 | Brown et al. | |
| 5,238,922 | 8/1993 | Graham et al. | |
| 5,245,061 | 9/1993 | Singh. | |
| 5,260,465 | 11/1993 | Singh et al. | |
| 5,260,479 | 11/1993 | Singh. | |
| 5,326,773 | 7/1994 | Desolms et al. | |
| 5,340,828 | 8/1994 | Graham et al. | |
| 5,352,705 | 10/1994 | Deana et al. | |

OTHER PUBLICATIONS

De Bernardi, M., et al., "Fungal Metabolites XXIV*: Recent Chemical Investigations of Basidiomycetes Triterpenes and Their Biological Activities," Latinoamer. Quim vol. 20/2, pp. 57–64 (1989).

De Bernardi, M., et al., "Fungal Metabolites. IX. Triterpenes from *Naematoloma Sublateritium*," J. Nat. Products, vol. 44, pp. 351–356 (1981).

Gibbs, J.B., et al., "Selective Inhibition of Farnesyl–Protein Transferase Blocks Ras Processing in Vivo," The Jour. of Biol. Chem., vol. 268, No. 11, pp. 7617–7620 (1993).

Goldstein, J.L., et al., "Nonfarnesylated Tetrapeptide Inhibitors of Protein Farnesyltransferase," The Jour. of Biol. Chem., No. 24, pp. 15575–15578 (1991).

Ikeda, M., et al., "Isolation and Structure of Fasciculol A, a New Plant Growth Inhibitor from *Neamatoloma fasciculare*," Agric. Biol. Chem., vol. 41 (8), pp. 1539–1541 (1977).

James, G.L. et al., "Benzodiazepine Peptidomimetics: Potent Inhibitors of Ras Farnesylation in Animal Cells", Science, vol. 260, pp. 1937–1942 (1993).

Kikuchi, T., et al., "Syntheses of 24,25–Dideoxy–Fasciculol–A and Fasciculol–A, Constituent of *Naematoloma Fasciculare* (Fr.) Karst, A Poisonous Bitter Mushroom," Chem. Ltrs., pp. 1495–1498 (1979).

Kohl, N.E. et al., "Protein farnesyltransferase inhibitors block the growth of ras–dependent tumors in nude mice", Proc. Natl. Acad. Sci., USA, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Kubo, I., et al., "Calmodulin Inhibitors from the Bitter Mushroom *Naematoloma fasciculare* (Fr.) Karst. (Strophariaceae) and Absolute Configuration of Fasciculols," Chem. Pharm Bull., vol. 33, pp. 3821–3825 (1985).

Pompliano, D.L., et al., "Steady–State Kinetic Mechanism of Ras Farnesyl: Protein Transferase", Biochemistry, vol. 31, pp. 3800–3807 (1992).

Qian, T., et al., "Design and Structural Requirements of Potent Peptidomimetic Inhibitors of p21 ras Farnesyltransferase", The Journal of Biol. Chem., vol. 269, No. 17, issue of Apr. 29, pp. 12410–12413 (1994).

Reiss, Y., "Inhibition of Purified p21ras Farnesyl:Protein Transferase by Cys–AAX Tetrapeptides", Cell, vol. 62, pp. 81–88 (1990).

Reiss, Y. et al., Sequence requirement for peptide recognition by rat brain p21 ras protein farnesyltransferase, (1991) Proc. Natl. Acad. Sci. USA, 88, pp. 732–736.

Ruzicka, L., et al., "Observations on Triterpenes (Part 96) Proof of the Identity of Lanosterol and Kryptosterol," Helv. Chim. Acta, vol. 28, 759, pp. 1–8 (1945).

Schaber, M.D., et al., "Polyisoprenylation of Ras in Vitro by a Farnesyl–Protein Transferase", The Journ. of Biol. Chem., vol. 365, No. 25, pp. 14701–14704 (1990).

Schulz, S. and Nyce, J.W., "Inhibition of protein farnesyltransferase: a possible mechanism of tumor prevention by dehydroepiandrosterone sulfate," Carcinogenesis, vol. 15, No. 11, pp. 2649–2652 (1994).

(List continued on next page.)

*Primary Examiner*—Kimberly J. Prior
*Attorney, Agent, or Firm*—David A. Muthard; Mark R. Daniel

[57] ABSTRACT

The present invention is directed to steroidal or terpenoidal compounds which inhibit farnesyl-protein transferase (FPTase). The invention is further directed to chemotherapeutic compositions containing the compounds of this invention and methods for inhibiting farnesyl-protein transferase and treatment of cancer. The compounds of this invention have the following structure:

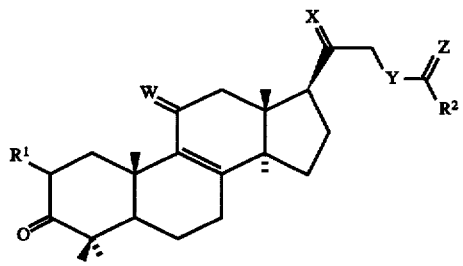

7 Claims, No Drawings

OTHER PUBLICATIONS

Simonsen, J. and Ross, W.C.J., "The Triterpenes and their Derivatives Hydrocarbons, Alcohols, Hydroxy–aldehydes, Ketones and Hydroxy–ketones," The Terprnes, vol. IV, pp. 39–115 (1957).

Singh, S.B., et al., "Fusidienol: A Novel Inhibitor of Ras Farnesyl–Protein Transferase from *Fusidium griseum*," Tetrahedron Letters, vol. 35, No. 27, pp. 4693–4696 (1994).

Suzuki, K., et al., "The Toxic Principles of *Naematoloma Fasciculare*," Chem. Pharm. Bull., vol. 31 (6) pp. 2176–2178 (1983).

Takahashi, A., et al., "Fasciculic Acids A, B and C as Calmodulin Antagonists from the Mushroom *Naematoloma fasciculare*," Chem. Pharm. Bull., vol. 37 (12) pp. 324703250 (1989).

Tinto, W.F. and John, L.M.D., "Triterpenoids of *Jatropha Gossypiifolia*," Jour. of Nat. Products, vol. 55, No. 6, pp. 807–809 (1992).

Tetrahedron, vol. 48, No. 33, pp. 6793–6798 (1992).

Steroids, vol. 53/3–5, pp. 579–596 (Mar.–May 1989).

Archives of Biochemistry and Biophysics, vol. 300, No. 2, Feb. 1, pp. 724–733 (1993).

INHIBITORS OF FARNESYL-PROTEIN TRANSFERASE

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Most of the inhibitors of farnesyl-protein transferase (FPTase) that have been previously described are in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)).

Several non-peptidyl natural products having farnesyl-protein inhibitory properties have also been described. For example, inhibitors of farnesyl protein transferase which are citrionic acid derivatives have been isolated as fermentation products from a strain of Chaetomella acutiseta (U.S. Pat. No. 5,260,465 and EP-547671-A). Synthetic analogs of those compounds have also been described (U.S. Pat. Nos. 5,245,061 and 5,260,479). Several other natural product farnesyl-protein transferase inhibitors have recently been described (S. B. Singh et al., Tetrahedron Letters, 35:4693–4696 (1994); S. B. Singh et al., J. Am. Chem Soc., 116:11606–11607 (1994)).

Recently, a steroidal analog has been reported that inhibited the farnesylation of a peptide corresponding to the C-terminus of K-Ras protein (S. Schulz and J. W. Nyce, Carcinogenesis, 15:1649–1652 (1994)).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes natural product compounds, their derivatives and related compounds having steroidal or terpenoidal structures which inhibit farnesyl-protein transferase, chemotherapeutic compositions containing the compounds of this invention, and methods for producing the compounds of this invention.

The compounds of this invention are illustrated by the following formula:

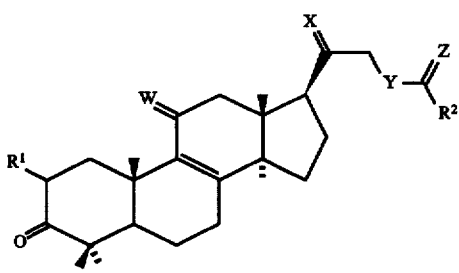

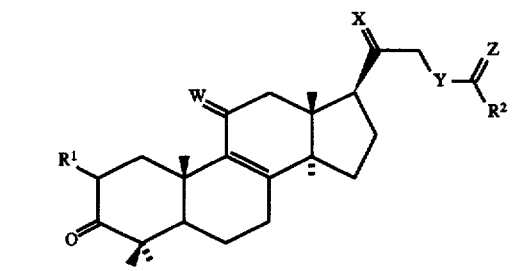

DETAILED DESCRIPTION OF THE INVENTION

The compounds of this invention are useful in the inhibition of farnesyl-protein transferase. In a first embodiment of this invention, the compounds which are inhibitors of farnesyl-protein transferase are illustrated by the formula I:

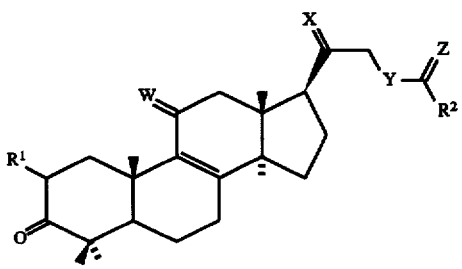

wherein:

$R^1$ is:
a) hydrogen;
b) —OH; or c)
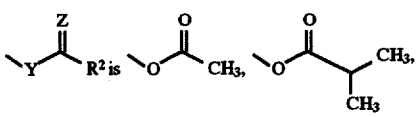

$R^2$ is hydrogen or $C_{1-4}$ alkyl;
  wherein the $C_{1-4}$ alkyl is optionally substituted with —OH of $CO_2R^3$;
$R^3$ is hydrogen or $C_{1-4}$ alkyl;
W is O or $H_2$;
X is O or (H, $CH_3$);
Y is O or —$(CH_2)_n$—;
Z is O, $C(CH_3)_2$ or (H, OH); and
n is 1 or 2;

and the pharmaceutically acceptable salts thereof.

In a second embodiment of this invention, the compounds are illustrated by the formula I:

wherein:

$R^1$ is:
a) hydrogen;
b) —OH; or c)
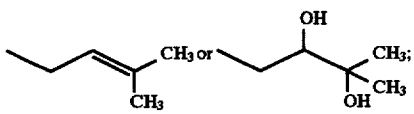

$R^3$ is hydrogen or $C_{1-4}$ alkyl;

W is O or $H_2$; and
X is O or (H,$CH_3$);

and the pharmaceutically acceptable salts thereof.

In a third embodiment of this invention, the compounds are illustrated by the formula I:

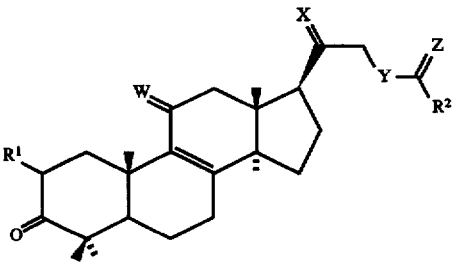

wherein:

$R^1$ is:
a) —OH; or
b)
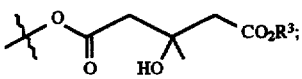

$R^3$ is hydrogen or $C_{1-4}$ alkyl;

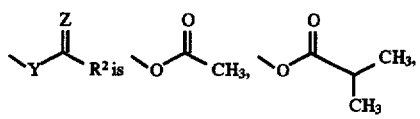

-continued

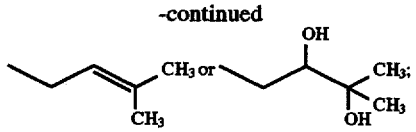

W is O or $H_2$; and
X is O or (H,CH$_3$);
and the pharmaceutically acceptable salts thereof.

In a fourth embodiment of this invention, the compounds are illustrated by the formula Ia:

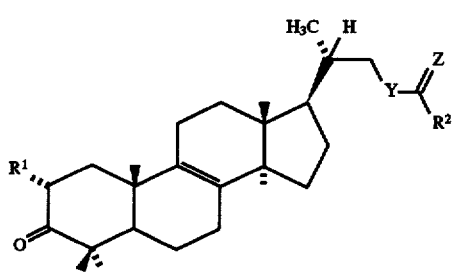

wherein:
$R^1$ is:
a) —OH; or
b)

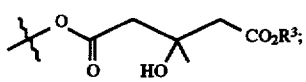

$R^3$ is hydrogen or $C_{1-4}$ alkyl;

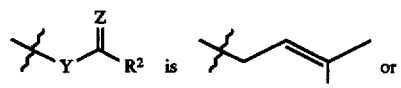

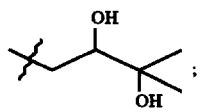

and the pharmaceutically acceptable salts thereof.

The following are specific examples of the compounds of the instant invention:

(2α)-2-(4-carboxy-3-hydroxy-3-methyl-1-oxobutoxy)-24,25-dihydroxylanost-8-en-3-one;

which is also known by the trivial name clavaric acid:

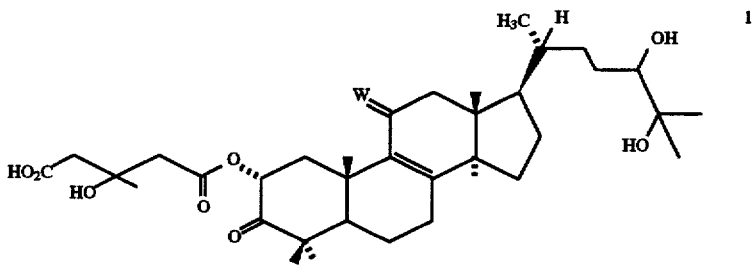

(2α)-2-hydroxy-24,25-dihydroxylanost-8-en-3-one;
which is also known by the trivial name clavarinone:

and
lanost-8,24-dien-3-one (3);

In the compounds of the present invention, combinations of substituents/or variables are permissible only if such combinations result in stable compounds.

As used herein, "alkyl" is intended to include both branched and straight-chain saturated aliphatic hydrocarbon groups having the specified number of carbon atoms. The term "alkyl" includes methyl, ethyl, propyl, iso-propyl, butyl, sec-butyl, tert-butyl and the like.

The pharmaceutically acceptable salts of the compounds of this invention include the conventional non-toxic salts of the compounds of this invention as formed, e.g., from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylene-diamine, trimethylamine, piperidine, pyrrolidine, benzylamine and the like, or a quaternary ammonium hydroxide such as tetramethylammonium hydroxide and the like.

The pharmaceutically acceptable salts of the compounds of this invention can be synthesized from the compounds of this invention which contain a acid moiety by conventional chemical methods. Generally, the salts are prepared by reacting the free acid with stoichiometric amounts or with an excess of the desired salt-forming inorganic or organic base in a suitable solvent or various combinations of solvents.

The compound 1 may be prepared in an aerobic fermentation procedure employing a novel culture, MF-6001, obtained by culturing the internal tissue of a mushroom identified as *Clavariadelphus truncatus*. Although the use of this organism is specifically described herein, mutants of the above described organism are also capable of producing the compounds of this invention.

The culture MF-6001 is that of an basidiomycetes isolated from internal tissues of fruitbodies of basidiomycetes found in Cercedilla in Madrid, Spain. This culture was deposited on Dec. 8, 1994 with the American Type Culture Collection at 12301 Parklawn Drive, Rockville, Md. 20852 as ATCC 74314.

The following is a general description of culture MF-6001:

Colonies 50–52 mm in diameter after 2 weeks on oatmeal agar (Difco) at 25° C., 85% relative humidity, 12 hours photoperiod. Aerial mycelium appressed, felty, forming radial strands, with margin even, slightly raised, floccose, minutely fimbriate. Colony color white to yellowish white at the center, white at the margin (color names from Kornerup, A. & Wanscher, J. H., *Methuen handbook of colour*, London 1989). Reverse yellowish white, cream at the margin. Odors and exudates absent.

Colonies 23–25 mm in diameter after 2 weeks on potato dextrose agar (Difco) at 25° C., 85% relative humidity, 12 hours photoperiod. Aerial mycelium appressed, felty, with margin uneven, appressed to slightly raised, minutely fimbriated. Colony color white to yellowish white, greyish orange at the center, white at the margin. Reverse yellowish white to pale yellow (cream), light yellow, greyish orange or apricot. Odors and exudates absent.

Colonies 35–39 mm in diameter after 2 weeks on yeast-malt extract agar (10 g malt extract, 2 g yeast extract, 20 g agar in 1 liter distilled water) at 25° C., 85% relative humidity, 12 hours photoperiod. Aerial mycelium appressed, sparsely floccose, with margin uneven, submerged. Colony color pale yellow (cream) to greyish yellow (sand), white at the margin. Reverse apricot to golden yellow. Odors and exudates absent.

The mycelium is composed of undifferentiated hyphae, branched, septate, 2.5–4.0 μm in diameter, hyaline in water and KOH. Short irregular branches or knob-like protuberances are often present. The hyphae show autofluorescence, located in the cytoplasm, when viewed under the microscope of fluorescence. After 3–4 weeks of incubation the culture develops abundant arthrospores by fragmentation of the aerial mycelium. Arthrospores are hyaline, one-celled, cylindrical, occasionally slightly bent, 3.2–9.0×2.0–3.3 μm in size.

The compound 1 may also be prepared in an aerobic fermentation procedure employing a novel culture, MF-6060, obtained by culturing the internal tissue of a mushroom identified as *Clavariadelphus pistillaris*. Although the use of this organism is specifically described herein, mutants of the above described organism are also capable of producing the compounds of this invention.

The culture MF-6060 is that of a basidiomycetes isolated from internal tissues of fruitbodies of a mushroom found in a mixed forest in Viso del Marqués in Ciudad Real, Spain. This culture was deposited on Dec. 8, 1994 with the American Type Culture Collection at 12301 Parklawn Drive, Rockville, Md. 20852 as ATCC 74313.

The following is a general description of culture MF-6060:

Colonies 44–47 mm in diameter after 2 weeks on oatmeal agar at 25° C., 85% relative humidity, 12 hours photoperiod. Aerial mycelium appressed, felty, forming radial strands, with margin even, slightly raised, floccose, minutely fimbriate. Colony color white, yellowish white to pale yellow at the center, with some irregular radial areas light orange, greyish orange to brownish orange, white at the margin. Reverse white to yellowish white, with some irregular radial areas golden yellow, light orange or brownish yellow. Odors and exudates absent.

Colonies 19–22 mm in diameter after 2 weeks on potato dextrose agar at 25° C., 85% relative humidity, 12 hours photoperiod. Aerial mycelium appressed, sparsely floccose, with margin uneven, submerged. Colony color white to yellowish white. Reverse light orange to orange yellow at the center, white to yellowish white at the margin. Odors and exudates absent.

Colonies 23–27 mm in diameter after 2 weeks on yeast-malt extract agar at 25° C., 85% relative humidity, 12 hours photoperiod. Aerial mycelium appressed, sparsely floccose, with margin uneven, submerged. Colony color white, yellowish white to orange white. Reverse maize yellow to light yellow at the center, white to yellowish white at the margin. Odors and exudates absent.

The mycelium is composed of undifferentiated hyphae, branched, septate, 2.5–4.0 μm in diameter, hyaline in water and KOH. Short irregular branches or knob-like protuberances are often present, as well as irregular terminal and intercalary swellings of the hyphae, which can reach up to 14 μm broad. After 3–4 weeks of incubation the culture develops abundant arthrospores by fragmentation of the aerial mycelium. Arthrospores are hyaline, one-celled, cylindrical, occasionally slightly bent, 3.2–9.0×2.0–3.3 μm in size, in some cases arranged in coiled chains.

Based on the characteristics mentioned above, the identity of the cultures can not be inequivocally stated, but it is reasonably likely that the organisms represent the vegetative states of the related basidiomycetes *Clavariadelphus truncatus* and *Clavariadelphus pistilaris*. Both cultures are quite similar in pigmentation, texture of the mycelial mat, radial growth rates and microscopic morphology, which would be consistent with this idea. However, it should be pointed out that because of the absence in the literature of any previous description of these two basidiomycetes in pure culture, to which compare the strains described above, the precise scientific identification of the organisms is uncertain. It may be important that clamps have not been found. The formation of clamps, hyphal structures connecting contiguous cells, is a character exclusive of basidiomycetes, although not always present. Also, the presence of arthroconidia, knob-like protuberances and swellings in the hyphae are frequent in many genera of Aphyllophorales (Stalpers, J. A., "Identification of wood-inhabiting fungi in pure culture", *Studies in Mycology* 16, C. B. S., Baarn), and the macroscopical morphology of the instant colonies is also consistent with the appearance of many basidiomycetes in culture.

Compounds of this invention can be obtained by culturing the above noted microorganism in aqueous nutrient media containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone,casein acid hydrolysate, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 20 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as propylene glycol (P-2000®), polyalkylene glycol, polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 5 days. When growth is plentiful, usually 2 to 5 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 22 days. The fermentation is conducted aerobically at temperatures ranging from 20° to 40° C. To obtain optimum results, the temperatures are in the range of 22° to 28° C., most preferably 25° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

A mixture of an alcoholic solvent and an oxygenated solvent, such as an ester or a ketone, is employed to extract a compound(s) of this invention from the fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is methylethylketone. After concentrating the initial extract, the preferred solvent is methanol.

The chromatographic separations may be carried out by employing conventional column chromatography with ionic or nonionic absorbents or resins. Silica gel, such as that available from E. Merck, is the preferred adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification.

Reactions used to generate the compounds of this invention from commercially available starting materials (e.g.; lanosterol—Sigma Chemical) or from products of the above described fermentations are well known in the art (see, for example, Fieser and Fieser, *Steroids*, Reinhold (1957); Simonsen and Ross, *The Terpenes*, Vol. IV, Cambridge University Press (1957) and Ourisson, Crabbé and Rodig, *Tetracyclic Triterpenes*, Holden-Day (1964)). Thus, the instant compounds may be prepared by employing reactions shown in the Reaction Schemes 1–3 in addition to other standard manipulations such as ester hydrolysis, cleavage of protecting groups, etc., as may be known in the literature or exemplified in the experimental procedures. The Reaction Schemes are meant to be illustrative and are not limiting. It is understood that certain substituents present in intermediate compounds may not be compatible with reaction conditions illustrated in the Reaction Schemes. However, it is also understood that one of ordinary skill in the art will be able to utilize protecting groups well known in the art to allow incorporation of such substituents.

These reactions may be employed in a linear sequence to provide the compounds of the invention.

Synopsis of Reaction Schemes 1–3

As shown in Reaction Scheme 1, a 3-acetoxy steroid of formula 1, such as the acetate of commercially available lanosterol, and the like, may be hydrolyzed and then cautiously oxidized with chromic acid or dehydrogenated with copper powder to provide the compound of the instant invention of formula Ia. Alternative oxidation conditions include an Oppenauer oxidation, a Swern oxidation and the like. The olefinic lanosterol-type sidechain may be protected as the 24,25-dibromo adduct prior to such an oxidation.

Alternatively, the acetoxy compound may be oxidized with excess chromic acid to provide the dione 5, which may then be selectively reduced to provide the 11-keto compound 6, as shown in Scheme 1. Deprotection and careful oxidation of compound 6 provides the compound of the invention Ib.

Synthetic manipulation of the C-17 side chain to produce compounds of the instant invention is illustrated in Reaction Scheme 2. Thus, the side-chain of lanosterol is degraded to the 17-acetyl compound 11. This intermediate may then be derivatized by standard synthetic manipulations.
The lanosterol-type unsaturated side chain may also be converted to the diol as illustrated in Reaction Scheme 3.
Reaction Scheme 1
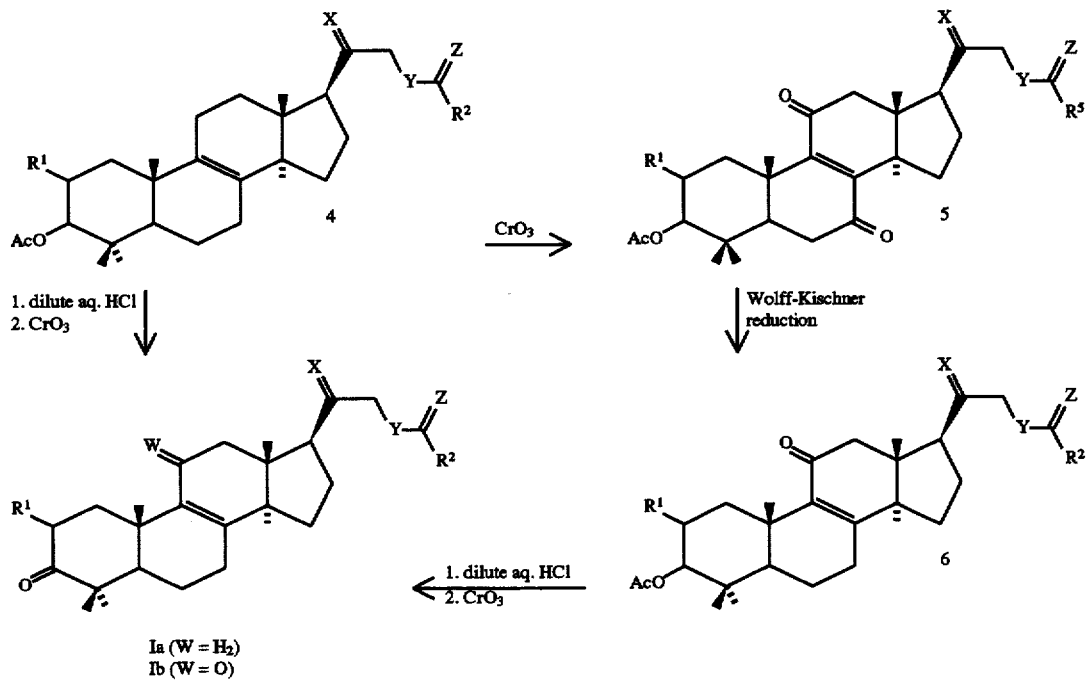
Reaction Scheme 2
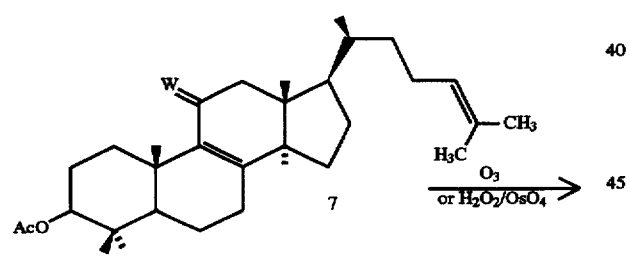
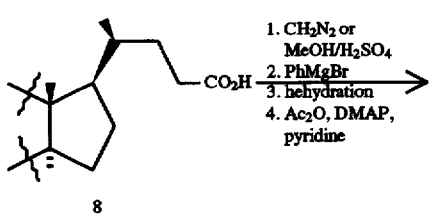
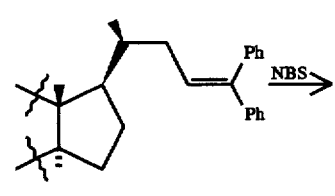
-continued
Reaction Scheme 2
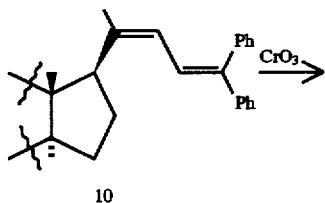
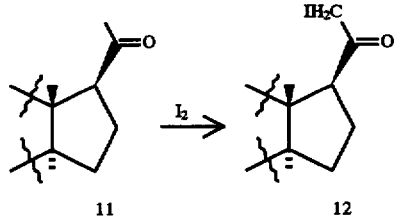
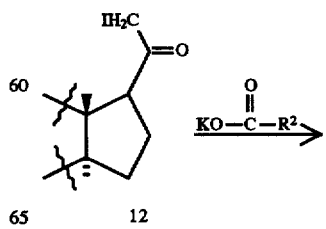

-continued
Reaction Scheme 2

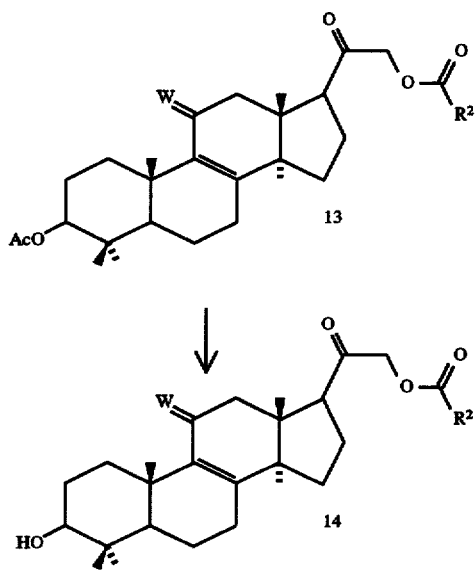

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

Reaction Scheme 3

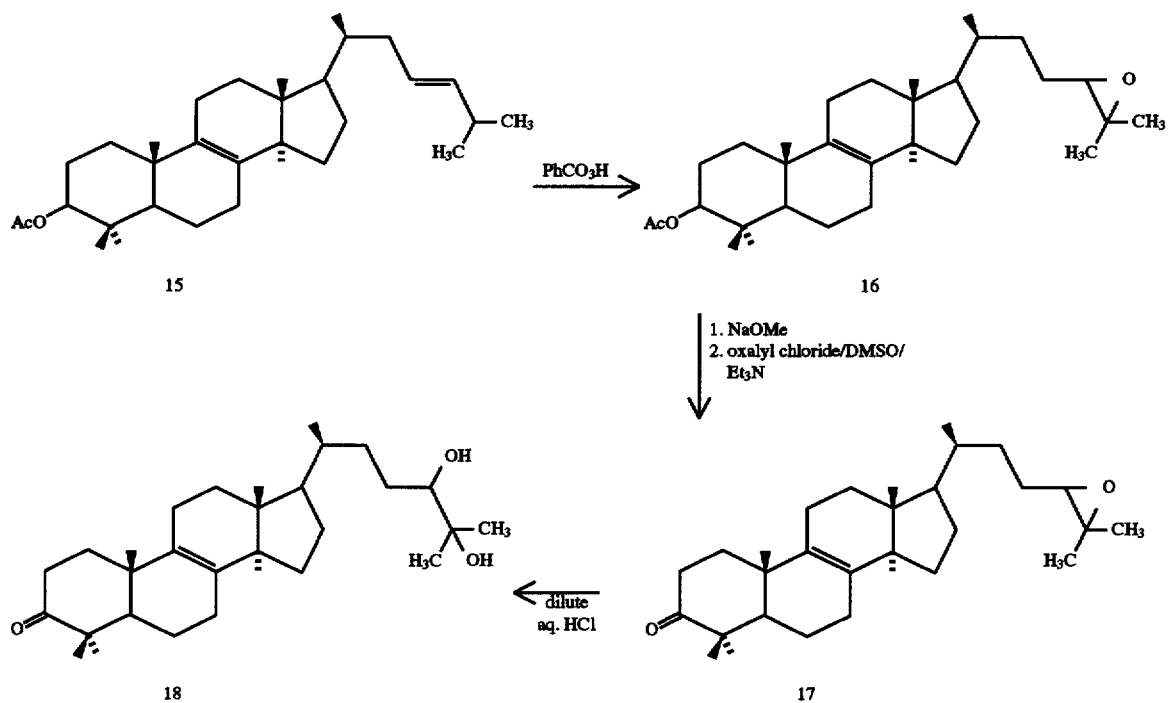

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compound 1 by Fermentation of MF-6001

A. Culturing MF-6001

The indetermined hyphomycete culture was maintained in sterile soil and stored at 4° C. until ready for use. The seed culture was inoculated by aseptically transferring a small mount of the preserved soil into a 250 ml Erlenmeyer flask containing 50 mls of seed medium of the following composition (in g/liter); corn steep liquor, 5.0; tomato paste, 40.0; oat flour, 10.0; glucose, 10.0; and trace elements solution, 10 mls/liter (consisting of, in g/liter: $FeSO_4.7H_2O$, 1.0; $MnSO_4.4H_2O$, 1.0; $CuCl_2.2H_2O$, 0.025; $CaCl_2.2H_2O$, 0.1; $H_3BO_3$, 0.056; $(NH_4)_6MoO_{24}.4H_2O$, 0.019$ZnSO_4.7H_2O$, 0.2; dissolved in 0.6N HCl). Seed medium was prepared with distilled water, the pH was adjusted to 6.8 by adding NaOH and the medium dispensed into 250 ml Erlenmeyer flasks and capped with cotton plugs before being autoclaved at 121° C. for 20 minutes. The seed culture was incubated at 25° C., on a gyrotory shaker (220 rpm, 5.1 cm throw) for 144–150 hours prior to the inoculation of fermentation flasks.

Fermentations were performed on solid substrate production medium formulated as follows: millet, 15.0 g/250 mls Erlenmeyer flask to which was added 15 mls medium of the following composition prepared with distilled water, (in g/flask) 0.5 g yeast extract, 0.1 g sodium tartrate, 0.5 g sucrose, 0.5 g alfalfa, 0.1 g corn oil and 0.01 g $FeSO_4.7H_2O$. Solid substrate production flasks were capped with cotton plugs and sterilized at 121° C. for 15 minutes. Immediately prior to inoculation, 15.0 mls of distilled water was added to each flask, and the flasks were resterilized at 121° C. for 20 minutes. Each production flask was inoculated with 2.0 mls of vegetative seed growth mixed throughout the solid substrate. Production flasks were incubated without agitation at 250° C. for 21 days. Individual flasks were extracted with 50 mls MEK (methyl ethyl ketone), shaken for 30 minutes and pooled.

EXAMPLE 2

Preparation of Compound 1 by Fermentation of MF-6060

A. Culturing MF-6060

The MF-6060 culture was maintained as a slant of potato dextrose agar and stored at 4° until ready for use. The seed culture was inoculated by aseptically transferring the upper third of the slant culture into a 250 ml Erlenmeyer flask containing 50 mls of seed medium of the following composition (in g/liter); corn steep liquor, 5.0; tomato paste, 40.0; oat flour, 10.0; glucose, 10.0; and trace elements solution, 10 ml/liter (consisting of, in g/liter; $FeSO_4•7H_2O$, 1.0; $MnSO_4•4H_2O$, 1.0; $CuCl_2•2H_2O$, 0.025; $CaCl_2•2H_2O$, 0.1; $H_3BO3$, 0.056; $(HN_4)_6MoO_{24}•4H_2O$, 0.019; $ZnSO_4•7H_2O$, 0.2; dissolved in 0.6N HCl). Seed medium was prepared with distilled water, the pH was adjusted to 6.8 by adding NaOH and the medium dispensed into 250 ml Erlenmeyer flasks and capped with cellulose plugs before being autoclaved at 121° C. for 20 minutes. The seed culture was incubated at 25° C., on a gyratory shaker (220 rpm, 5.1 cm throw) for 144–150 hours prior to the inoculation of fermentation flasks.

Fermentations were performed in 250 ml Erlenmeyer flasks containing 45 mls of a liquid production medium formulated as follows: sucrose, 80 g/l; corn meal (yellow), 50 g/l; yeast extract, 1 g/l; distilled water, 1 liter. The flasks were capped with cellulose plugs and sterilized at 121° C. for 20 minutes. Each production flask was inoculated with 2.0 mls of vegetative seed growth. Production flasks were incubated without agitation at 25° C. for 14 days. Individual flasks were extracted with 40 mls MEK (methyl ethyl ketone), shaken for 30 minutes and pooled.

Presence of Compound 1 in the crude extracts was confirmed by HPLC analysis in comparison with Compound 1 isolated as described in Example 3.

EXAMPLE 3

Isolation of Compound 1

The solid fermentation product from Example 1 was extracted with methylethylketone, filtered and evaporated to produce 5 g of residue. The residue was dissolved in 200 ml of methanol and was loaded on a 1.5l sephadex LH-20 column which was eluted with methanol. The active fractions eluted in a broad band between 0.94–1.18 L of elution volumes of methanol. The combined active fractions were reduced on the rotovap to produce a brown residue (1.1 g). A portion of this residue (50 mg) was purified on a reverse phase Zorbax RX C-8 HPLC column (22.4×250 mm) using acetonitrile/water with 0.1% TFA (40:60) at a flow rate of 7 ml/min. Compound 1 eluted as a broad peak at 30–36 mins under a wavelength of 210 nm. Concentration of the fractions containing the desired compound provided Compound 1 as a white powder.

Physical properties of Compound 1
FABMS: (+) m/z 619(M+H), 641(M+Na)
HR-FAB: (+) 618.4019(calcd. for C36H58O08:618.4091)
IR (ZnSe)√max: 3600–3100(broad), 2972, 1716, 1681, 1388, 1203, 1149 cm$^{-1}$.
$^1$H and $^{13}$C NMR of Compound 1 in CDCl$_3$.

| # | δC | Type | δH |
|---|-----|------|------|
| 1 | 210.16 | CO | |
| 2 | 172.11 | CO | |
| 3 | 170.71 | CO | |
| 4 | 135.77 | C | |
| 5 | 132.80 | C | |
| 6 | 78.74 | CH | 3.35, brt |
| 7 | 73.33 | C | |
| 8 | 73.15 | CH | 5.706, dd, 13.4, 4.2 |
| 9 | 70.10 | C | |
| 10 | 52.38 | CH | |
| 11 | 50.49 | CH | |
| 12 | 49.80 | C | |
| 13 | 48.53 | C | |
| 14 | 45.33 | CH2 | 2.74, d, 16 |
| 15 | 45.05 | CH2 | 2.70, d, 16 |
| 16 | 44.53 | C | |
| 17 | 42.33 | CH2 | 2.30, dd, 12.4, 6 |
| 18 | 37.91 | C | |
| 19 | 36.24 | CH | |
| 20 | 33.06 | CH2 | |
| 21 | 30.75 | CH2 | |
| 22 | 30.69 | CH2 | |
| 23 | 28.34 | CH2 | |
| 24 | 28.26 | CH2 | |
| 25 | 27.14 | CH3 | 1.48 |
| 26 | 26.58 | CH3 | 1.17 |
| 27 | 26.05 | CH2 | |
| 28 | 24.48 | CH3 | 1.09 |
| 29 | 24.32 | CH3 | 0.86 |
| 30 | 23.25 | CH3 | 1.22 |
| 31 | 21.49 | CH2 | |
| 32 | 21.06 | CH3 | 1.18 |
| 33 | 19.94 | CH3 | 1.37 |
| 34 | 18.86 | CH2 | |
| 35 | 18.55 | CH3 | 0.92, d, 6 |
| 36 | 15.78 | CH3 | 0.72 |

EXAMPLE 4

Preparation of Compound 2 by hydrolysis of Compound 1
Sodium hydroxide (0.6 ml of 2% solution) was added to a cooled solution of Compound 1 (10.0 mg) in ethanol(1.0 ml) and the solution was stirred overnight at room temperature. The reaction mixture was diluted with water and extracted with ether. The ether extract dried and evaporated to produce Compound 2 as a white powder.

Physical properties of Compound 2
IR (ZnSe)√max: 3600–3100(broad), 2975, 1722, 1382, 1108 cm$^{-1}$.
$^1$H NMR of Compound 2 in CDCl3.

| | | |
|---|---|---|
| 1 | 0.72 | |
| 2 | 0.87 | |
| 3 | 0.94 | d, J = 6 |
| 4 | 1.12 | |
| 5 | 1.17 | |
| 6 | 1.22 | |
| 7 | 1.23 | |
| 8 | 1.26 | |
| 9 | 1.26–2.3 | m |
| 10 | 3.35 | t, J = 6 |

EXAMPLE 5

In vitro inhibition of farnesyl-protein transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl)piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CB$_q$/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nm Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <50 μM.

EXAMPLE 6

In vivo Ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 mM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 7

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula I:

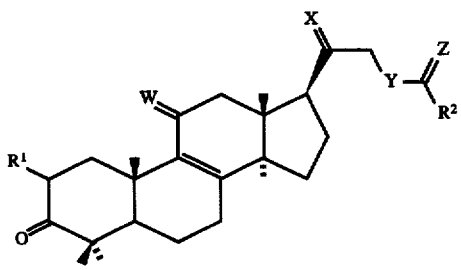

wherein:

R$^1$ is:

a) —OH; or b)

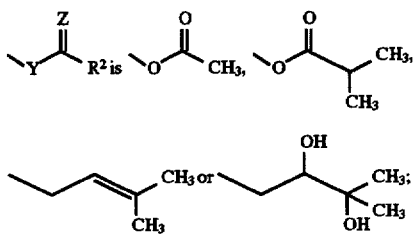

R$^3$ is hydrogen or C$_{1-4}$ alkyl;

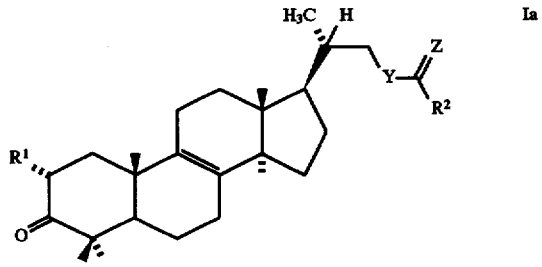

W is O or H$_2$; and
X is O or (H,CH$_3$);

or a pharmaceutically acceptable salt thereof.

2. The compound according to claim 1 which inhibits farnesyl-protein transferase of the formula Ia:

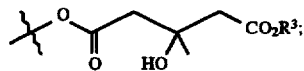

wherein:

R$^1$ is:

a) —OH; or b)

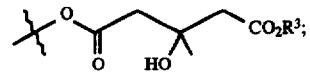

R$^3$ is hydrogen or C$_{1-4}$ alkyl;

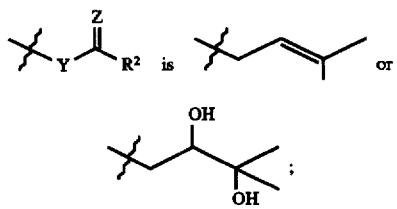

or a pharmaceutically acceptable salt thereof.

3. The compound according to claim 1 which is:
(2α)-2-(4-carboxy-3-hydroxy-3-methyl-1-oxobutoxy)-24,25-dihydroxylanost-8-en-3-one;

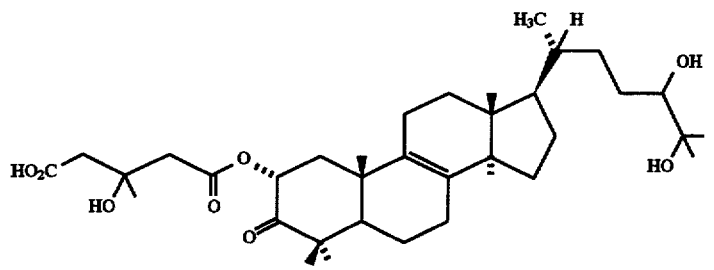

or a pharmaceutically acceptable salt thereof.

4. A pharmaceutical composition comprising a pharmaceutical carrier, and dispersed therein, a therapeutically effective amount of a compound of claim 3.

5. The compound according to claim 1 which is: (2α)-2-hydroxy-24,25-dihydroxylanost-8-en-3-one;

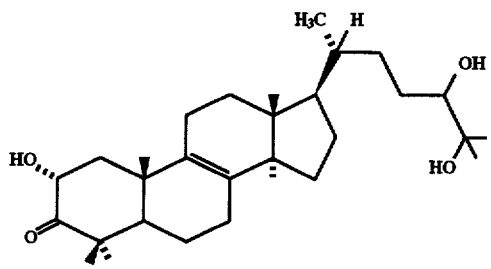

or a pharmaceutically acceptable salt thereof.

6. A pharmaceutical composition comprising a pharmaceutical carrier, and dispersed therein, a therapeutically effective amount of a compound of claim 5.

7. A pharmaceutical composition comprising a pharmaceutical carrier, and dispersed therein, a therapeutically effective amount of a compound of claim 1.

* * * * *